United States Patent [19]

Ohnemus et al.

[11] Patent Number: 5,527,284
[45] Date of Patent: Jun. 18, 1996

[54] SINGLE USE SYRINGES

[75] Inventors: Randall E. Ohnemus, 9648 Halifax St., Ventura, Calif. 93004; Craig W. Smith; Thomas C. Kuracina, both of Ventura, Calif.

[73] Assignee: Randall E. Ohnemus, Ventura, Calif.

[21] Appl. No.: 245,447

[22] Filed: May 18, 1994

[51] Int. Cl.⁶ .................................................. A61M 5/00
[52] U.S. Cl. .............................................. 604/110; 604/236
[58] Field of Search ..................................... 604/110, 187, 604/218, 236, 237, 238

[56] References Cited

U.S. PATENT DOCUMENTS

2,893,390  7/1959  Lockhart .................................. 604/238
3,159,159  12/1964  Cohen ...................................... 604/236
4,832,693  5/1989  Gloyer ..................................... 604/110

Primary Examiner—John D. Yasko
Attorney, Agent, or Firm—Thomas C. Kuracina

[57] ABSTRACT

A single use syringe in which the single use aspects are accomplished by a lumen spike which is forced into the lumen bore to seal the passageway from the syringe body to the hypodermic needle. Fail-safe characteristics to prevent bypassing the single use provisions are provided by having a frangible area of the endwall holding the lumen break out at a force less than that required to force the lumen spike out of the lumen bore. This aspect can also be used to improve other approaches to single use syringes. The lumen spike can be formed as part of the piston/plunger and the piston/plunger can be a unitary device useful in all syringes.

4 Claims, 5 Drawing Sheets

SINGLE USE SYRINGES

BACKGROUND OF THE INVENTION

This invention relates to medical syringes with hypodermic needles and, more particularly, to apparatus for sealing a lumen bore of a syringe lumen communicating between an interior of a syringe body and a hypodermic needle carried by the lumen to prevent a second use of the syringe comprising, a lumen spike moveable by a plunger/piston of the syringe between a retracted position allowing fluid to flow from the interior of the syringe body to the hypodermic needle and a sealing position disposed within the lumen bore preventing fluid from flowing from the interior of the syringe body to the hypodermic needle. In a single use syringe having a lumen bore of a syringe lumen communicating over a connecting path between an interior of a syringe body and a hypodermic needle carried by the lumen and a valve member blocking the connecting path after a first use of the syringe to prevent a second use of the syringe it also relates to a fail-safe improvement for preventing the connecting path from being subsequently unblocked to allow more than one use of the syringe comprising, a portion of the syringe body carrying the lumen and the valve member when the valve member is blocking the connecting path being frangible when subjected to a force $f_1$ thereby separating the lumen from the syringe body; and, the valve member being resistive against unblocking the connecting path to a force $f_2$ which is greater than $f_1$ whereby the portion of the syringe body will fracture and separate the lumen from the syringe body before the valve member unblocks the connecting path. It further relates to a unitary plunger/piston for use in a cylindrical syringe body of internal diameter $d_1$ comprising, a plastic plunger shaft portion having an integral cylindrical piston portion of a diameter $d_2$ equal to or smaller than $d_1$ formed at an inner end thereof; and, annular sealing means of a diameter $d_3$ greater than $d_1$ carried by the piston portion for compressing against internal sidewalls of the syringe body.

Needle-borne pathogens such as staph, hepatitis-B, and HIV have made single use syringes a virtual necessity. Even in areas where needles are provided free to illegal drug users, there is a problem with multiple uses of needles. Users high on drugs or in need of an injection simply will not take the time to get a new needle. And, unfortunately, sometimes the free needles are not available or available in necessary quantities. Whatever the reasons, it is a problem that must be faced.

Some public health areas are also facing problems of multiple needle use, even among medical workers. Whether by accident or intent, the use of a syringe on more than one patient is simply not something that can be tolerated in the presence of the many needle-transmitted pathogens that can be present in today's environment.

Single use syringes, per se, are not new technology. There are several factors that must be considered, however, and present technology does not satisfy all the necessary criteria. Price is probably the single most important factor. While not too many years ago all injections were done with reusable metal and glass syringes and replaceable needles that were intended to be autoclaved between uses, virtually all injections are now performed with single use plastic syringes that sell for only a few cents each and are intended to be disposed of after use. Thus, to be financially viable, single use syringes must not add very much to the selling price. If not mandated by law, a single use syringe that is over a threshold price acceptable to the financial interests determining what is bought and what is not, will not be purchased. If mandated by law, the financial interests will mandate that the lowest price syringe meeting the letter of the law be purchased—whether it works well for its intended purpose or not. While not an ideal situation, those are simply the facts of life which must be faced by anyone trying to solve the ultimate problem.

Particularly because of the illegal drug users, a viable single use syringe must be absolutely one-use in design and not merely inconvenient to reuse. If it can be made to work again, the illegal drug user will do so. After price, this should be the most important factor to anyone actually trying to solve the ultimate problem. This means that if a single use syringe can be made to work again, the drug user will make it work. Single use syringes must also be considered from two perspectives. There is a need for syringes that can be provided directly to illegal drug users which can only be used once. There is also a need for syringes that are used by others and then disposed of, which may fall into the hands of illegal drug users either intentionally or unintentionally. And, the problems are not the same. It can be assumed that medical workers, diabetics, and the like, will follow the designated protocol for use of a syringe. Thus, they should activate any single use provisions incorporated into the syringe. Such syringes should not be given directly to illegal drug users as they will most likely be instructed by someone who has figured it out, how to use the syringe without activating the single use provisions. Ideally, syringes given directly to illegal drug users should activate upon use in any manner, even if the injection is partially or totally incomplete as a result of misuse.

Finally, those syringes intended for medical use and not first use by illegal drug users must be normally usable; that is, it must be able to function in its normal manner when employed for its single use. A 3 cc syringe that can only be used for up to 1 cc and acceptable to an illegal drug user is simply not acceptable for the general medical marketplace.

In this regard, while it is the illegal drug users and a few others that are causing the problem and requiring a solution, in order to be effective against the few, the whole community of injection users is going to have to adapt to new technology. If a source of multiple-use needles remains, the drug-users will get them—either directly by stealing or by creating an expanded illegal industry in needle trafficking. For example, one recent unconfirmed report stated that a "clean" needle can bring up to twenty dollars in New York City. Thus, users like diabetics will be forced to pay more for their needles and will have to use single-use needles to prevent the subsequent sale of their used needles to illegal drug.

As will be seen from the discussion of the prior art that follows, it is virtually impossible to come up with a single use syringe that is both economically feasible and absolutely fail-safe in the hands of an illegal drug user as the first user. Thus, it makes more sense to address the larger problem of a single use syringe that is both economically feasible and absolutely fail-safe in the hands of an illegal drug user (or anyone at all for that matter) as a second-in-time potential user.

Several known prior art syringes related to this problem and its solution will now be discussed and their shortcomings identified.

U.S. Pat. No. 4,838,870 of Haber et al. is directed to a syringe in which the hypodermic needle is grabbed by the plunger at the bottom of its stroke so that as the plunger is withdrawn, the needle is pulled into the syringe body. The intent is to make it safe to dispose of the syringe since the needle is now housed within the syringe body. If one were to try to use the Haber et al. syringe as a single use syringe, the plunger could be removed and the needle reinserted if a used syringe. In either case (new or fixed), the gripping fingers could be snipped off to bypass the needle being withdrawn during further use.

A similar structure and situation exists with U.S. Pat. No. 5,125,899 to Frignoli. In this case, however, Frignoli intends that his syringe be a single use syringe. As with the Haber et al. syringe, however, a new Frignoli syringe could have its single use capability disabled relatively simply. A used Frignoli syringe might be slightly more difficult to reassemble; but, could probably be made at least usable for an illegal drug user's use with a pocket knife and perhaps a bit of glue. In this regard, it must be remembered that the regaining of functionality (and not beauty or sanitation) is the end goal of the drug user.

PCT/FR90/00826 is a simple and inexpensive approach to solving the problem. The syringe nozzle has an external barbed front portion frangibly attached to the back portion. The needle hub has internal barbs that permanently attach it to the front portion. In use, an extension on the piston pushes the front portion and breaks the frangible attachment. If new when in the hands of the illegal drug user, snipping off the extension disables the single use aspects of the syringe. If used, the extension can be snipped off and then the needle hub reattached with silicone rubber adhesive, epoxy glue, or the like—easily stolen from a hardware or drug store.

PCT/AU91/00394 discloses a valve for a syringe intended to render it a single use device. A number of embodiments are disclosed. A first reaction is that regardless of how effective any or all of the embodiments are, the cost of manufacture and sale will be too high to be salable in the marketplace if there is a less costly substitute. It would also appear that the valve could be disabled by driving a nail, ice pick, or the like, through it from the lumen. It must be remembered that all that is required to reestablish functionality is to make the valve leak.

Bartlett et al. (U.S. Pat. No. 5,254,093) is like PCT/AU91/00394 above. The cost of manufacture and sale would be prohibitive as against any simple and cheap device that works at all. It also appears that a resourceful individual with a pocket knife and a little glue could amputate the valving arrangement and reattach the needle to the end of the syringe body. Such an approach might be ugly, but it should be functional.

U.S. Pat. No. 5,000,735 of Whelan employs both a ball valve and a disconnecting piston to render the subject syringe single use. As with other valves, all that is required is to make the valve seat leak. A nail or ice pick could to that quite nicely even if the ball remained trapped. And, the plunger could be reattached with a bit of silicone rubber adhesive. As another observation, the valve 94 could not be molded by inexpensive molding techniques. Thus, if manufacturable at all, the cost of manufacture would be prohibitive to successful sales.

The apparatus of Jaffe et al. disclosed in U.S. Pat. No. 5,067,942 is another example of high cost of manufacture. The hypodermic needle has a closed inner end with side ports that are covered by a retractable sleeve. Once the syringe has been used, the retracting mechanism for the sleeve is disabled so that the ports remain covered. Hypodermic needles are manufactured in large volumes by automated machinery designed to take lengths of tubing, cut them to length, and sharpen one end to a bevel. They are not designed to seal the opposite end and put a port through the sidewalls. That factor alone would make the Jaffe et al. syringe design financially undesirable to any major manufacturer of syringes.

The approach of Yerman in U.S. Pat. No. 4,233,975 is the closest prior art to the approach of the present invention as will be seen. Yerman has a male member carried by the opening to the lumen. When the plunger is depressed, it forces the male member into the opening to the hypodermic needle thereby blocking it from further use. There are several embodiments including one in which the end of the piston acts as the sealing member and the piston becomes detached from the plunger. As with many of the above-described approaches, Yerman disposes a valve mechanism over the opening to the needle. Thus, like the other needles with valves, all that is required is to make the valve leak to work. The Yerman syringe could also be disabled as to its single use function by inserting a long screw into the body after removing the piston, threading it into place, and pulling out the parts interfering with normal operation. The various embodiments as depicted would also be difficult to impossible to injection mold inexpensively and, therefore, the Yerman syringe would not likely be financially viable.

Wherefore, it is the object of this invention to provide a low-cost and effective single use syringe.

It is another object of this invention to provide a single use syringe that cannot be reworked to make it reusable.

It is yet another object of this invention to provide a single use syringe that incorporates highly effective fail-safe provisions.

It is still another object of this invention to provide a single use syringe which functions by permanently blocking the fluid path to the hypodermic needle.

It is a still further object of this invention to provide a single use syringe that is first used by medical personnel or the like following accepted use protocols so as to completely and uniformly active the single use and fail-safe provisions of the syringe thereby preventing a second use of the syringe under virtually any circumstances.

Other objects and benefits of this invention will become apparent from the description which follows hereinafter when read in conjunction with the drawing figures which accompany it.

SUMMARY

The foregoing objects have been achieved by the apparatus of the present invention for sealing a lumen bore of a syringe lumen communicating between an interior of a syringe body and a hypodermic needle carried by the lumen to prevent a second use of the syringe comprising, a lumen spike moveable by a plunger/piston of the syringe between a retracted position allowing fluid to flow from the interior of the syringe body to the hypodermic needle and a sealing position disposed within the lumen bore preventing fluid from flowing from the interior of the syringe body to the hypodermic needle.

In the preferred embodiment, the lumen spike has a body portion with first gripping means for holding the body portion in the lumen bore. In one version, the first gripping means comprises a plurality of gripping teeth which dig into sidewalls of the lumen in another version, the lumen bore has second gripping means for engaging the first gripping means. In one implementation thereof, the second gripping means comprises a socket and the first gripping means comprises a ball snap-fitted into the socket. In another implementation thereof, the second gripping means comprises an internal shoulder at a top end of the lumen bore and the first gripping means comprises an external shoulder on the body portion abutting the internal shoulder.

The preferred fail-safe embodiment additionally comprises a portion of the syringe body carrying the lumen being frangible when subjected to a force $f_1$ thereby separating the lumen from the syringe body; and, the first gripping means holds the body portion of the lumen spike in the lumen bore against a force $f_2$ which is greater than $f_1$ whereby the portion of the syringe body will fracture and separate the lumen from the syringe body before the body portion of the lumen spike moves towards the retracted position in the lumen bore. This aspect of the present invention can also be employed with other single-use syringes to provide fail-safe characteristics thereto.

According to one aspect of this invention, the lumen spike has a sealing head portion blocking an entry opening to the lumen bore when the lumen spike is in the sealing position. The sealing head portion may cover the entry opening external to the lumen bore. The sealing head portion may also cover the entry opening internal to the lumen bore.

The lumen spike may be disposed within the lumen bore in both the retracted position and the sealing position. The lumen spike may also be attached to and carried by the plunger/piston. In one approach, the lumen spike is integral to a piston portion of the plunger/piston. In another approach, the lumen spike is integral to a plunger portion of the plunger/piston.

DESCRIPTION OF THE PREFERRED EMBODIMENTS

Figure 1:
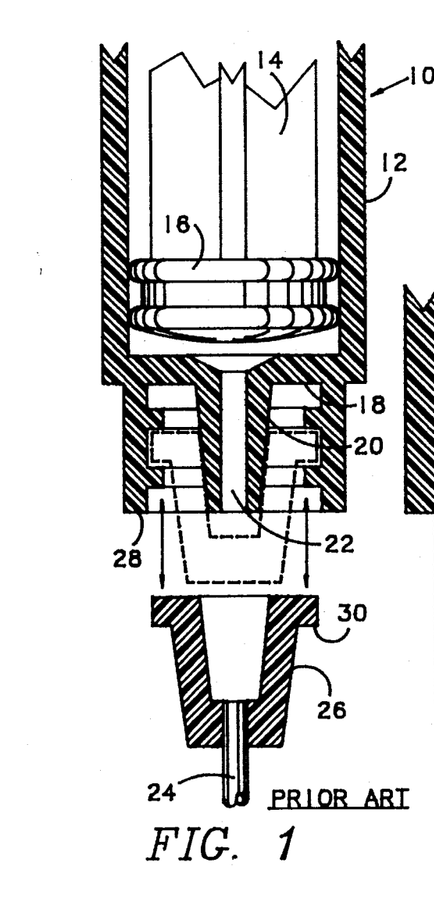
FIG. 1 is a simplified partially cutaway side view drawing of a prior art hypodermic syringe wherein the needle is removably carried by a so-call luer-lock fitting.

A typical prior art disposable syringe 10 is depicted in FIG. 1. There is a cylindrical syringe body 12 having a plunger 14 with a cylindrical sealing piston 16 on the end thereof. The endwall 18 of the body 12 has a lumen 20 with a central bore 22 communicating with the interior of the body 12. A hypodermic needle 24 carried by a fitting 26 attaches to the lumen 20. Because of problems associated with injection molding the plastic body 12 and attempting to simultaneously mold a hypodermic needle 24 directly into the endwall 18, the needle 24 is not molded into the endwall 18. In the cheapest of disposable syringes, the fitting 26 snaps onto the lumen 20. In the majority of syringes, the fitting 26 threadedly attaches into a so-called luer-lock socket 28 surrounding the lumen 20 by means of ears 30 on the fitting 26. In the drawing figures herein, a luer-lock attachment of the hypodermic needle 24 is depicted since it is the most familiar configuration to medial workers and others of ordinary skill in the art.

Like many of the prior art approaches, the present invention is directed to cutting off the fluid flow from the syringe body 12. While the prior art techniques can be bypassed by anyone truly bent on doing so as described above, as will be seen from the drawings and description which follows, in its preferred embodiments the present invention will destroy the syringe 10 from further use before it will allow itself to be bypassed.

In the days of muzzle loading cannon, a huge cannon could be completely disabled by a process called "spiking". The cannon had a small bore communicating from the rear to the chamber at the back of the large main bore containing the gunpowder and cannon ball. To fire the cannon, a small quantity of gunpowder was pored in the small bore and a flame touched to the outer end. The flame traveled down the small bore and ignited the main charge within the cannon's main bore thereby firing the cannon ball. To disable the cannon, a metal spike or nail was hammered into the small bore. Unless and until the spike could be removed, the cannon was useless. The present invention works on the same principle by "spiking" the bore 22 within the lumen 20.

Figure 2:
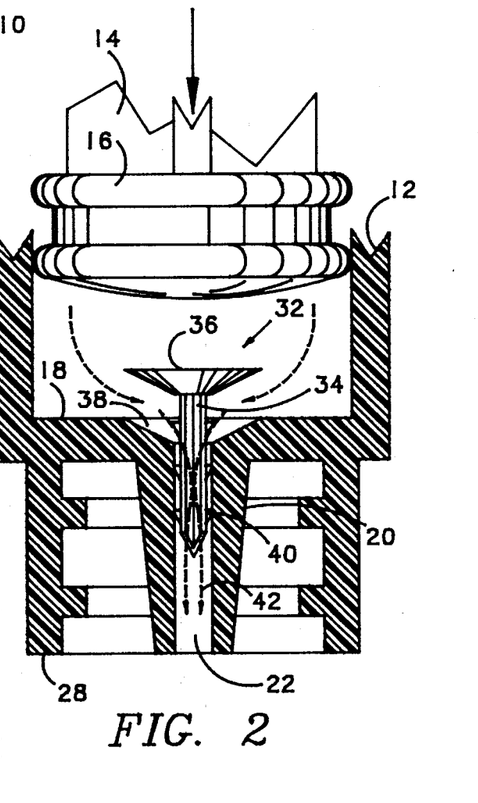
FIG. 2 is a simplified partially cutaway side view drawing of a hypodermic syringe in the area of the luer-lock fitting according to the present invention in a first embodiment employing a lumen spike disposed in the lumen and retracted for first-time use of the syringe.
Figure 3:
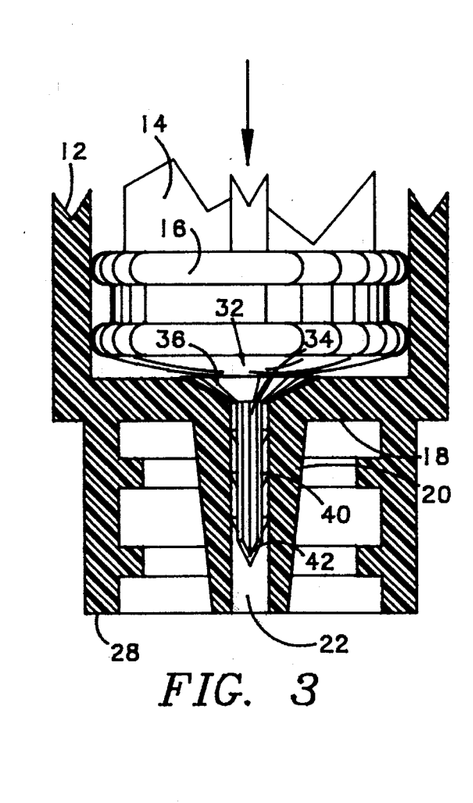
FIG. 3 shows how the lumen spike of FIG. 2 is fully embedded in the lumen and seals the syringe from further use when the syringe plunger is pushed to the bottom of the syringe body.

In a first embodiment as depicted in FIGS. 2 and 3, the lumen spike 32 comprises a body 34 having a sealing head 36 at the top shaped to fit the opening 38 to the lumen 20 in the endwall 18. The body 34 is V-shaped in cross section and has gripping teeth 40 along its length. The gripping teeth 40 are angled to allow the body 34 to be pressed into the lumen bore 22 by the piston 16, but dig into the plastic of the lumen 20 to prevent the body from being withdrawn easily. At the manufacturer, the lumen spike 32 is pressed into the lumen bore 22 in a retracted position as depicted in FIG. 2. Fluid within the syringe body 12 is free to flow past the sealing head 36 and down the bore 22 past the V-shaped body 34 as depicted by the dashed lines 42. As the piston 16 is pressed toward the endwall 18 in use, the piston 16 pushes against the sealing head 36 and pushes it into sealing engagement with the opening 38. The lumen 20 is thus "spiked" against further use.

Figures 4, 5, 6, 7, 8, 9, 10:
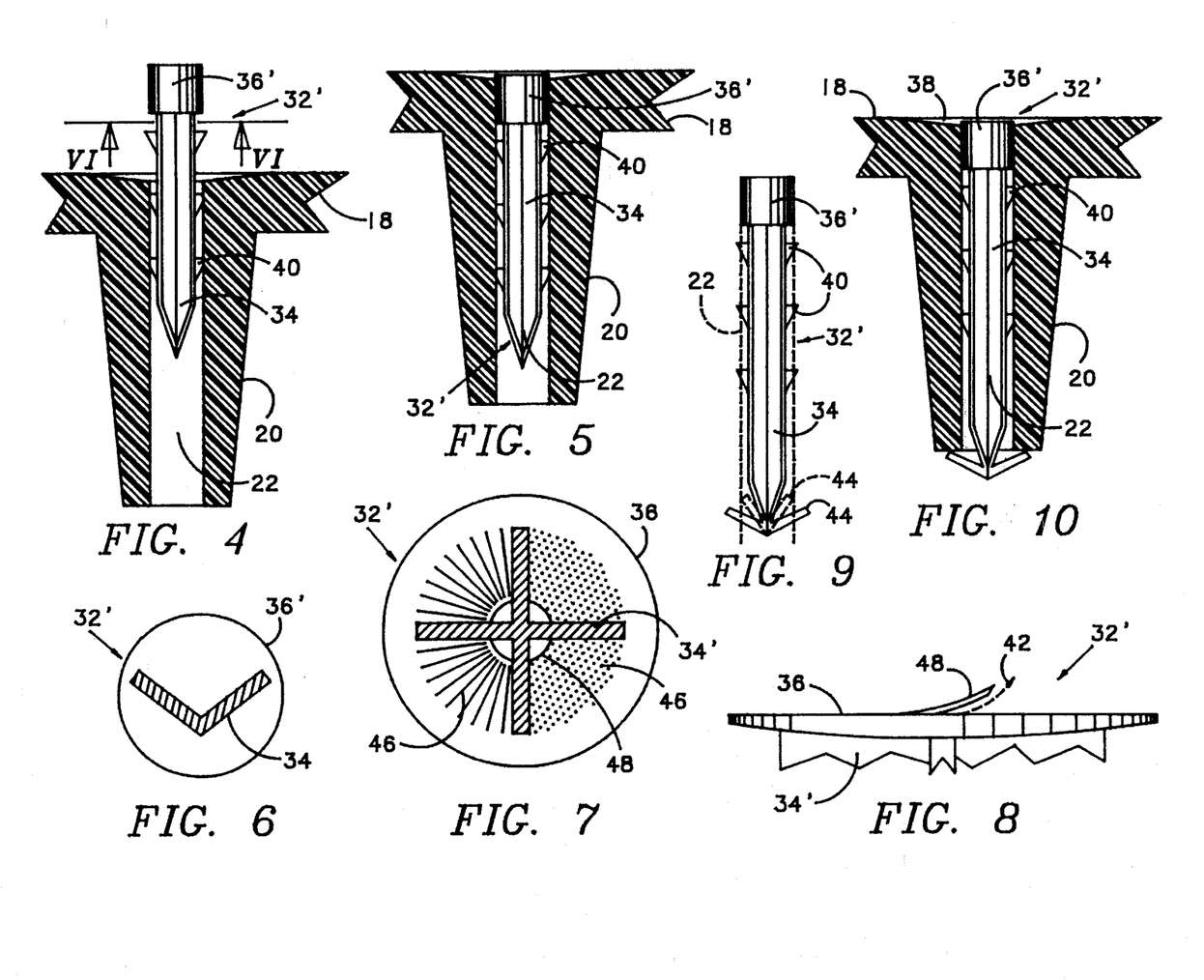
FIG. 4 is an enlarged cutaway drawing of a syringe lumen with a second embodiment lumen spike of the present invention disposed in the lumen and retracted for first-time use of the syringe.
FIG. 5 shows how the lumen spike of FIG. 4 is fully embedded in the lumen and seals the syringe from further use when the syringe plunger is pushed to the bottom of the syringe body.
FIG. 6 is a cross-sectional view of the lumen spike of FIGS. 2–5 in the plane VI—VI.
FIG. 7 is a cross-sectional view of and alternate approach to the lumen spike of FIGS. 2 and 3 along with out-gassing provisions that may be added to the sealing top portion.
FIG. 8 is a side view of the top portion of FIG. 7 showing an optional one-way valve that can be included therein.
FIG. 9 depicts the spike of FIGS. 4 and 5 with an additional locking end.
FIG. 10 shows how the lumen spike of FIG. 9 is fully locked in the lumen by the locking end.

A second embodiment of the lumen spike is depicted in FIGS. 4, 5, and 6 where it is designated as 32'. The body 34 is the same as the previous embodiment. The difference is in the sealing head 36'. In this embodiment, the sealing head 36' is cylindrical and of substantially the same diameter as the lumen bore 22. Thus, as depicted in FIG. 5, when the sealing head 36' is fully seated, it is pushed down into the bore 22 rather than just having a mating fit across the opening 38 as with the prior embodiment. The sealing of the bore 22 is thus more secure and more complete.

In any embodiment, if there is sufficient space between the end of the lumen 20 and the interior of the fitting 26, folding gripping hooks 44 can be provide on the end of the body 34. The hooks 44 are folded when within the bore 22 as depicted ghosted in FIG. 9 and expand to grip the end of the lumen 20 as depicted in FIG. 10.

These initial embodiments of the present invention can be made of metal or plastic. It is important to remember that either metal or plastic must be inert to the possible fluids to be used in the syringe 10 and tough enough with respect to the plastic of the lumen 20 that the teeth 40 will dig into the sidewalls of the lumen 20 as opposed to being sheared off by the lumen 20 at the opening 38.

Several variations and optional additions to the various embodiments of the present invention, as appropriate, are depicted in FIGS. 7 and 8. The V-shaped body 34 of FIG. 6 has only two rows of teeth 40. On the other hand, the material can be sized such as to put the body 34 under tension by compressing the sides of the "V" so as to give additional gripping power. As shown in FIG. 7, the body 34' can be X-shaped in cross section so as to have four rows of teeth 40. While not depicted, it could also be Y-shaped to provide three rows of teeth 40. If the sealing head 36 is of a diameter substantially equal to the inside diameter of the syringe body 12 for maximum sealing, one may want to have micro-fine openings 46 therethrough with a hinged section 48 for fluid/gas transfer and to allow fluid to be drawn into the syringe body 12.

While not specifically depicted, it may be desirable to have an indication on the spike 32 as to its position relative to being fully closed so that a user does not inadvertently spike the syringe 10 while attempting to fill it for use. This is more important with these first-described embodiments than with other embodiments yet to be described which take a definite force to spike them whereby it is less likely that they will be unintentionally spiked it may also be desirable to color the lumen 20 and the body 34 of the spike 32 so that there will be a visible color change when the syringe 10 has been completely spiked against further use. An indication on the syringe body 12 related to the position of the piston 16 may also be employed to prevent inadvertent seating of the spike 32 during filling of the syringe, if appropriate to the embodiment being employed and desired by the users.

Figure 11:
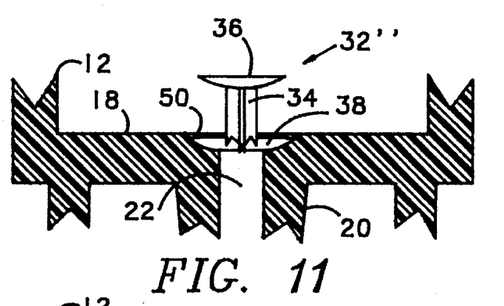
FIG. 11 is an enlarged cutaway drawing of a syringe lumen with a third embodiment lumen spike of the present invention disposed in the lumen and retracted for first-time use of the syringe.
Figure 12:
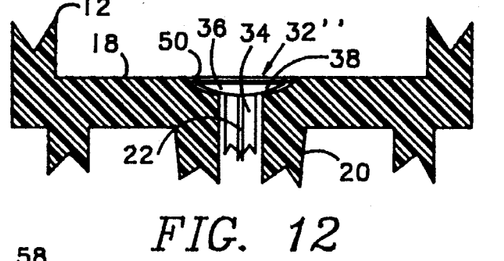
FIG. 12 shows how the lumen spike of FIG. 11 snaps into the top of the lumen when the syringe plunger is pushed to the bottom of the syringe body.

A third embodiment of the lumen spike, designated as 32" is shown in FIGS. 11 and 12. In this instance, a snap ridge 50 around the opening 38 receives and further holds the sealing head 36 in the manner of a snap fastener when the sealing head 36 is pressed into the opening 38. In this embodiment, the teeth 40 are still employed as the main source of holding power for the lumen spike 32.

While the first three embodiments employed teeth 40 on the body 34 of the spike 32 to hold the spike 32 in the bore 22, FIGS. 13–16 depict a fourth embodiment which is the first of several not employing teeth. It will also be realized that the first two embodiments can be implemented without modification of an existing syringe. That is, they can be added to an existing syringe. Like the third embodiment, the remaining embodiments disclosed herein require modification to one or more of the syringe components. It will be noted by those of ordinary skill in the art, however, that the modifications necessary to implement any of the embodiments of the present invention are easily accomplished by modifying the molds used for the injection molding process so that the present invention can be implemented in quantity with little or no additional manufacturing cost required.

Figure 13:
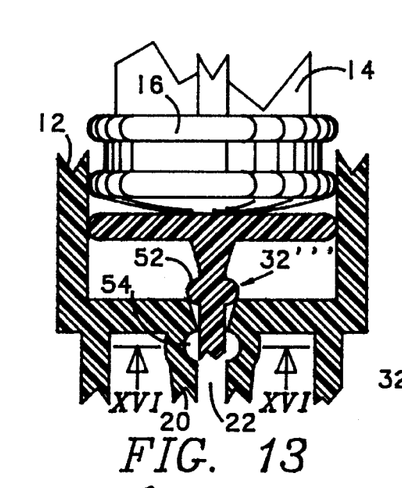
FIG. 13 is an enlarged cutaway drawing of a syringe lumen with a fourth embodiment lumen spike of the present invention disposed in the lumen and retracted for first-time use of the syringe.
Figure 14:
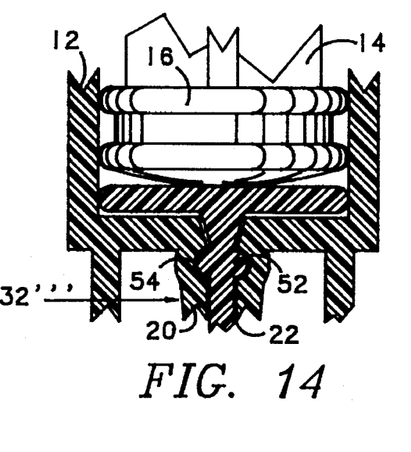
FIG. 14 shows how the lumen spike of FIG. 13 snaps into a retaining groove formed into the sidewalls at the top of the lumen when the syringe plunger is pushed to the bottom of the syringe body.
Figure 15:
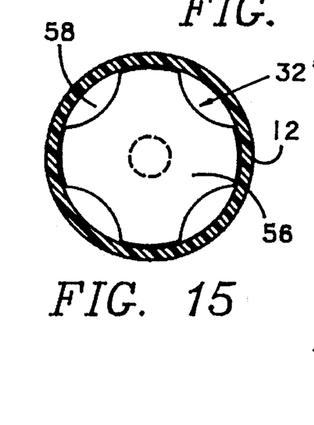
FIG. 15 is a top view of the top portion of the lumen spike of FIGS. 13 and 14.
Figure 16:
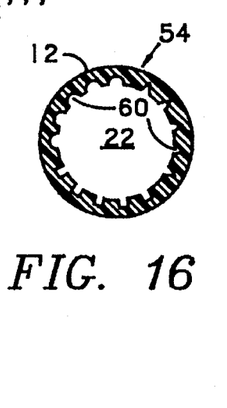
FIG. 16 is a cutaway drawing through the lumen of FIG. 13 in the plane XVI—XVI showing optional grooves that can be formed therein for fluid and gas passage.

The lumen spike 32'" of FIGS. 13 and 14 has a snap ridge 52 circumferentially about the top of a cylindrical body 34". The lumen bore 22 has a mating snap groove 54 formed therein. The polypropylene plastic typically used for the syringe body 12 has enough "give" and the parts are sized such that the snap ridge 52 can be pressed into a snap-fit with the groove 54 as the piston 16 is pressed towards the endwall 18 as depicted in FIG. 14. For alignment and retention purposes, it is preferred that the head 56 of the spike 32''' be cylindrical and of a diameter substantially equal to the inside diameter of the syringe body 12 and have fluid passages 58 therein as depicted in FIG. 15. It is also preferred that the groove 54 and surrounding area have some sort of fluid slots 60 as depicted in FIG. 16 so that the entry to the lumen bore 22 is not inadvertently sealed prematurely by the snap ridge 52.

Figure 17:
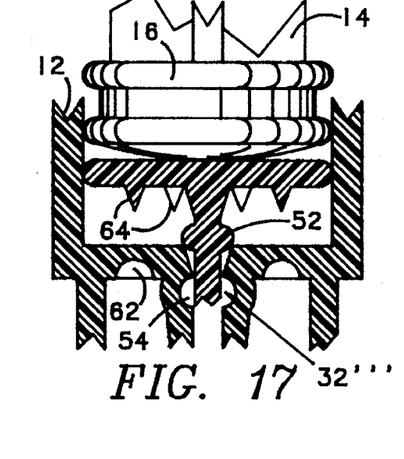
FIGS. 17 and 18 show the embodiment of FIGS. 13 and 14 with the addition of a frangible groove surrounding the lumen in the endwall of the syringe body and teeth for further weakening the endwall's frangible groove when the syringe has been used so that tampering and attempting to remove the spike will result in destruction of the syringe for further use as a syringe.
Figure 18:
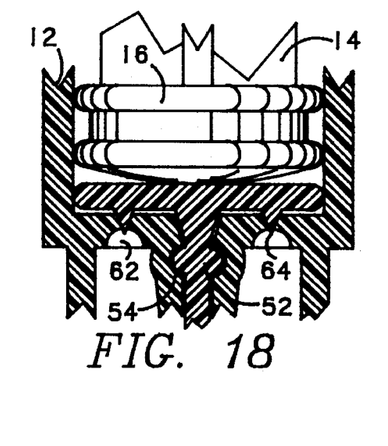

A preferred modification to be included in newly designed syringe bodies according to the present invention so as to implement the virtually fool-proof fail-safe aspects thereof is depicted in FIGS. 17 and 18. The endwall 18 surrounding the lumen 20 has a groove 62 formed therein to form a frangible area of the endwall 18. The idea is that the endwall 18 not be weakened enough that it will fail under normal injection use; but, that the holding power of the lumen spike 32 in the bore 22 is sufficient as compared with the force on the endwall necessary to break the lumen from the endwall 18 along the groove 62 is such that the endwall will break before the lumen spike 32 comes out of the bore 22. Thus, once the syringe 10 has been used and spiked, a nail or other elongated object driven into the lumen bore 22 to knock out the lumen spike 32 will first result in breaking the lumen 20 out of the endwall 18 thereby destroying the syringe 10 for all further use. If the lumen spike design employed is adaptable for the purpose (such as the embodiment of FIGS. 13 and 14 shown in FIGS. 17 and 18), the bottom of the head 56 can be provided with a plurality of teeth 64 that cut through the plastic at the bottom of the groove 62 and thereby weaken it so that it will fracture and destroy the syringe 10 much easier after use than before use.

As those of ordinary skill in the art will obviously recognize, this fail-safe aspect of the present invention can also be incorporated into some of the prior art described above so as to improve the fail-safe aspects thereof. For example, PCT/FR90/00826 could have the entire lumen (i.e. cylindrical mouthpiece 6) broken out by the extension 14 according to this aspect of the present invention thereby destroying the syringe from further use rather than allowing it to be reassembled easily with glue or other sealant. In Frignoli, the entire end of the syringe could be pulled out and made non-replaceable by using a frangible groove according to the present invention instead of a slip fit that can be reassembled. The Haber et al. apparatus could also be modified in like manner to make it a single use syringe instead of a self needle-storing syringe. The same is true of Yerman insofar as it can be manufactured inexpensively in any of his embodiments. The key is to destroy the syringe regardless of the primary single use techniques employed therein rather than let it be fixed for rouse.

For ease of manufacture and assembly, placing the lumen spike on the piston or plunger is probably easier and less costly than positioning it in the lumen. If standard automated assembly machines can be employed with modified components, the assembly costs are, of course, unaffected. If the components can be modified at minimal cost as by simply changing or modifying injection molds, that aspect is also minimized. The remaining embodiments take that approach.

Figure 19:
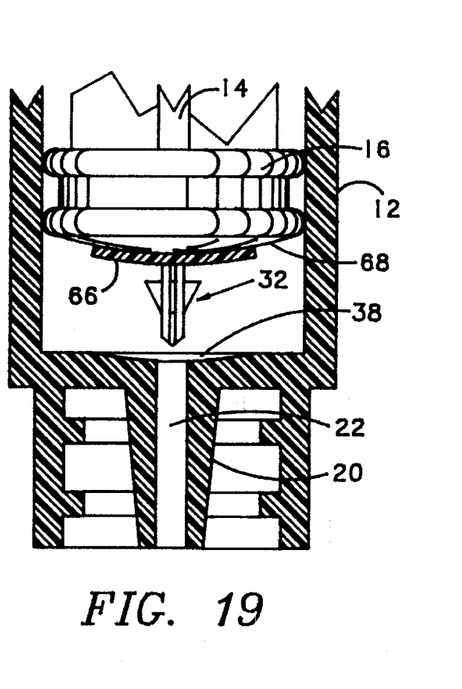
FIG. 19 is an enlarged cutaway drawing of a syringe lumen with a fifth embodiment lumen spike of the present invention carried by the syringe plunger and retracted from the lumen for first-time use of the syringe.

In the embodiment of FIG. 19, the syringe body 12 is standard. Optionally and preferred, however, the frangible groove 62 of FIGS. 17 and 18 is molded in for added fail-safe characteristics as described above. Note in this regard that as apparent to those of ordinary skill in the injection molding art, the groove 62 can be added with minor modification to the mold and no changes in the manner or difficulty of pulling the molded piece from the mold. In this simplest of approaches, the lumen spike 32 is carried by a base 66 shaped to fit the end 68 of the piston 16 and position the spike 32 concentrically over the opening 38 of the lumen bore 22. The base 66 can be attached with any of several appropriate adhesives known to those of ordinary skill in the art. As will be appreciated, the lumen spike 32 can be of any of the various shapes described previously or still to be described hereinafter.

Figure 20:
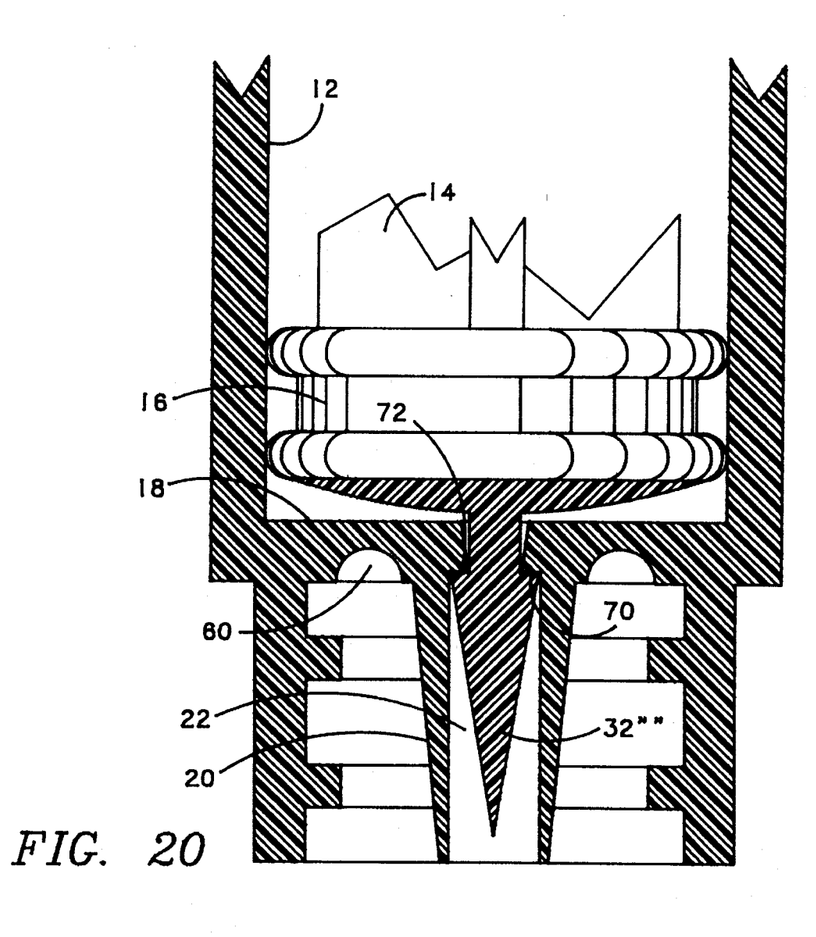
FIG. 20 is a greatly enlarged cutaway drawing of a syringe lumen with a sixth embodiment lumen spike of the present invention carried by the syringe plunger and wedged in the lumen after first-time use of the syringe and including a frangible groove surrounding the lumen in the endwall of the syringe body.

In the embodiment of FIG. 20, the lumen bore 22 has a shoulder 70 molded at the top periphery. As with the considerations of FIG. 16 described above, it may be desirable to mold slots into the shoulder 70 to prevent premature sealing of the lumen bore 22. The lumen spike 32'''' is like an inverted Christmas tree in cross section and is molded into the soft plastic (or rubber) of the piston 16'. As the lumen spike 32'''' advances with the piston, it is pushed through the shoulder 70 as it compresses and is lubricated by the fluid within the syringe being injected. As the piston 16' reaches the end of its stroke as depicted in FIG. 20, the shoulder 72 separating the top of the spike 32'''' from the narrower bottom passes beyond the shoulder 70 thereby locking the spike 32'''' within the lumen bore 22. Alternatively, the spike 32'''' and the lumen 22 could be configured like those of FIGS. 13, 14 and 17, 18. In either configuration, the spike 32'''' has a natural stopping point for syringe filling purposes and must have an addition force applied thereto at the end of the injection to seat and lock the spike 32''''. There should also be a tactile feel and a possible audible click to indicate to the user that the single use aspects have been activated. Note that the preferred frangible groove 62 is included within the modified mold producing the syringe body 12 for this embodiment. Thus, any attempt to force the spike 32'''' out of the lumen 22 will result in the plastic of the endwall 18 in the area of the groove 62 fracturing.

Figures 21, 22, 23, 24:
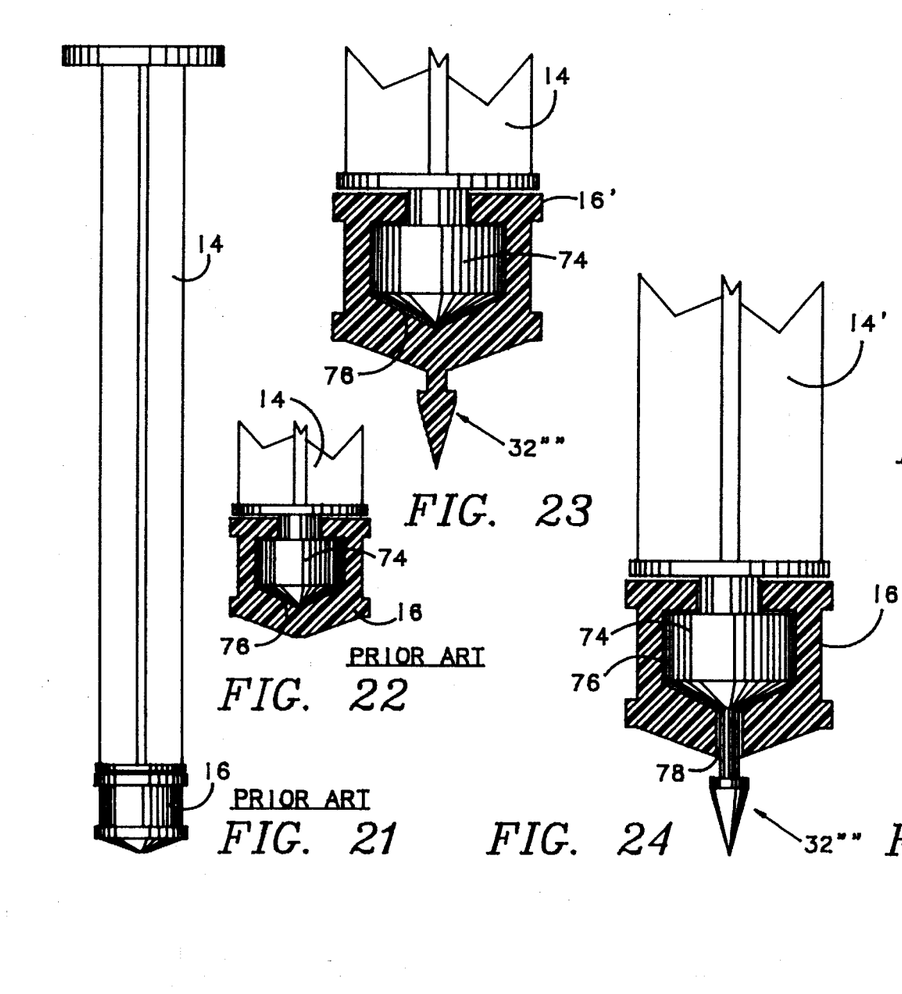
FIG. 21 is a side view of a prior art plunger and piston assembly as used in a typical syringe.
FIG. 22 is a cutaway view of the tip of FIG. 21 showing how the piston attaches to the plunger.
FIG. 23 is a cutaway view of a plunger tip with a piston according to the present invention and incorporating a lumen spike attached thereto.
FIG. 24 is a cutaway view of a plunger tip incorporating a lumen spike according to the present invention with a piston attached thereto wherein the spike passes through a bore in the piston provided therefor.

As depicted in FIGS. 21 and 22, prior art pistons 16 are snap fit onto the ends of their plungers 14 by a fitting 74 on the end of the plunger 14 being pressed into a mating socket 76 molded into the piston 16. Thus, it is a simple matter to modify the mold producing the piston 16 to provide the piston 16' of the embodiment of FIG. 20 as depicted in FIG. 23. As an alternative, the lumen spike 32'''' of FIG. 20 (in that configuration, the configuration of FIGS. 13, 14 and 17, 18, or any other desired configuration, could be molded onto the end of the plunger 14' and a bore 78 molded into the piston 16 for the spike 32'''' to pass through as depicted in FIG. 24.

Figure 25:
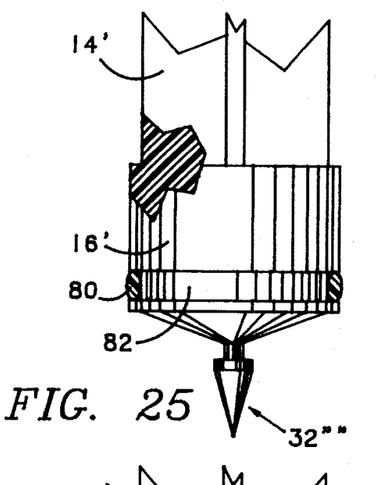
FIG. 25 is a partially cutaway view of a unitary plunger tip and piston incorporating a lumen spike according to the present invention and employing an O-ring for sealing purposes.
Figure 26:
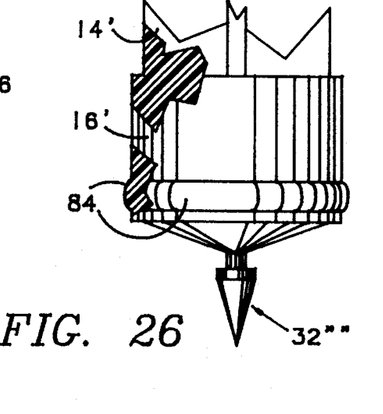
FIG. 26 is a partially cutaway view of a unitary plunger tip and piston incorporating a lumen spike according to the present invention and employing an integral sealing ring for sealing purposes.

Two other possible modifications to the plunger 14 and piston 16 are depicted in FIGS. 25 and 26. In FIG. 25, the plunger 14' and piston 16' along with the lumen spike 32'''' are an integral part molded of the plastic material of the plunger 14'. For sealing to the inside walls of the syringe body 12, an oval cross-sectioned O-ring 80 of a softer plastic (or rubber) material is carried by a groove 82 formed in the piston 16' portion of the unitary part.

In FIG. 26, the plunger 14' and piston 16' along with the lumen spike 32'''' are again an integral part. In this case, however, the injection molding process employs two plastic sources simultaneously injected into the mold to prevent a cold joint at their point of joining. The piston 16' and lumen spike 32'''' are molded of a soft plastic (or rubber) material while the plunger 14' is simultaneously molded of the usual harder plunger plastic. For sealing to the inside walls of the syringe body 12, the piston 16' has at least one sealing ridge 84 circumferentially formed into the outer surface as shown.

Wherefore, having thus described the present invention,

What is claimed is:

1. Apparatus for sealing the lumen bore of a syringe communicating directly between an interior of a syringe body and a hypodermic needle carried by an outer end of the lumen to prevent a second use of the syringe comprising:

a lumen spike disposed within the syringe body moveable by a plunger/piston of the syringe between a retracted position allowing fluid to flow from the interior of the syringe body to the hypodermic needle and a sealing position disposed within the lumen bore preventing fluid from flowing from the interior of the syringe body through the lumen bore to the hypodermic needle;

said lumen spike having a body portion with a gripping means for gripping sidewalls of the lumen bore and holding said body in the lumen bore; and said gripping means comprising a plurality of gripping teeth along said sides of said body portion which frictionally engage (dig into) said sidewalls of the lumen bore.

2. Apparatus for sealing the lumen bore of a syringe in claim 1 wherein:

said gripping teeth along said sides of said body portion dig into said sidewalls of the lumen bore to prevent movement of said body portion from a sealing position, 3. Apparatus for sealing the lumen bore of a syringe communicating directly between an interior of a syringe body and an outer end of the lumen to prevent a second use of the syringe comprising:

a lumen spike disposed within the syringe body moveable by a plunger/piston of the syringe between a retracted position allowing fluid to flow from the interior of the syringe body and a sealing position disposed within the lumen bore preventing fluid from flowing from the interior of the syringe body through the lumen bore;

said lumen spike having a body portion with a gripping means for gripping sidewalls of the lumen bore and holding said body in the lumen bore; and said gripping means comprising a plurality of gripping teeth along said sides of said body portion which frictionally engage (dig into) said sidewalls of the lumen bore.

4. Apparatus for sealing the lumen bore of a syringe in claim 3 wherein:

said gripping teeth along said sides of said body portion dig into said sidewalls of the lumen bore to prevent movement of said body portion from a sealing position.

* * * * *